(12) United States Patent
Xing et al.

(10) Patent No.: US 7,550,591 B2
(45) Date of Patent: Jun. 23, 2009

(54) IMATINIB PRODUCTION PROCESS

(75) Inventors: Liu Xing, Shanghai (CN); He Xungui, Shanghai (CN); Yuan Wang, Shanghai (CN); Michel Bekhazi, Pointe Claire (CA); Sonia Krivonos, Beer Sheva (IL); Edna Danon, Meitar (IL)

(73) Assignee: Chemagis Ltd., Bnei Brak (IL)

( * ) Notice: Subject to any disclaimer, the term of this patent is extended or adjusted under 35 U.S.C. 154(b) by 0 days.

(21) Appl. No.: 11/743,520

(22) Filed: May 2, 2007

(65) Prior Publication Data

US 2008/0275055 A1 Nov. 6, 2008

(51) Int. Cl.
*C07D 401/14* (2006.01)

(52) U.S. Cl. ........................................... 544/295
(58) Field of Classification Search .................. 544/295
See application file for complete search history.

(56) References Cited

U.S. PATENT DOCUMENTS

| | | | |
|---|---|---|---|
| 5,521,184 A | 5/1996 | Zimmermann et al. | |
| 6,894,051 B1 | 5/2005 | Zimmermann et al. | |
| 2005/0234069 A1 | 10/2005 | Parthasaradhi et al. | |
| 2006/0084628 A1* | 4/2006 | Pottage | 514/49 |
| 2006/0142580 A1 | 6/2006 | Loiseleur et al. | |
| 2006/0149061 A1 | 7/2006 | Anli et al. | |
| 2006/0173182 A1* | 8/2006 | Kankan et al. | 544/295 |
| 2006/0223816 A1 | 10/2006 | Adin et al. | |
| 2006/0223817 A1 | 10/2006 | Adin et al. | |

FOREIGN PATENT DOCUMENTS

| | | |
|---|---|---|
| EP | 0564409 A1 | 10/1993 |
| WO | 99/03854 A1 | 1/1999 |
| WO | 03/062220 A1 | 7/2003 |
| WO | WO 03/066613 A1 | 8/2003 |
| WO | WO 2004/074502 A2 | 9/2004 |
| WO | WO 2004/106326 A1 | 12/2004 |
| WO | WO 2005/075454 A2 | 8/2005 |
| WO | WO 2005/095379 A2 | 10/2005 |
| WO | WO 2006/024863 A1 | 3/2006 |
| WO | WO 2006/054314 A1 | 5/2006 |
| WO | WO 2007/023182 A1 | 3/2007 |

OTHER PUBLICATIONS

Li, et al., J. Biol. Chem., vol. 273, No. 51, Dec. 18, 1998, pp. 34230-34233.*

Kil et al., "Synthesis and positron emission tomography studies of carbon-11-labeled imatinib (Gleevec)," *Nuclear Medicine and Biology*, vol. 34, No. 2, pp. 153-163 (Feb. 2007).

* cited by examiner

*Primary Examiner*—Mark L Berch
*Assistant Examiner*—Cecilia M Jaisle
(74) *Attorney, Agent, or Firm*—Leydig, Voit & Mayer, Ltd.

(57) ABSTRACT

Provided is a process for producing imatinib and salts thereof, e.g., imatinib mesylate. The process includes reacting 4-(4-methyl-piperazin-1-ylmethyl)-benzoic acid with N-(5-amino-2-methylphenyl)-4-(3-pyridyl)-2-pyrimidine-amine in the presence of a carboxylic acid coupling reagent, to produce imatinib, and optionally converting the imatinib into a salt.

23 Claims, No Drawings

IMATINIB PRODUCTION PROCESS

BACKGROUND OF THE INVENTION

Imatinib (N-{5-[4-(4-methyl-piperazinomethyl)-benzoylamido]-2-methylphenyl}-4-(3-pyridyl)-2-pyrimidine-amine) is represented by the following structural formula (I):

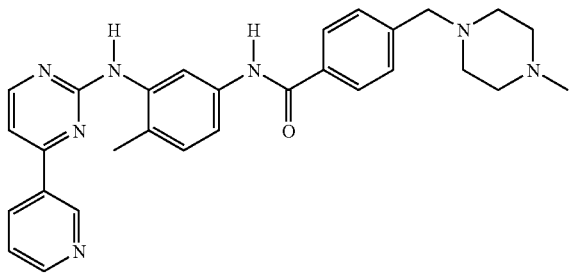

(I)

Imatinib is known as an inhibitor of tyrosine kinases and is indicated for the treatment of chronic myeloid leukemia (CML), Philadelphia chromosome positive leukemia, for patients in chronic phase and in blast crisis, accelerated phase and also for malignant gastrointestinal stromal tumors. It selectively inhibits activation of target proteins involved in cellular proliferation. Imatinib also has potential for the treatment of other cancers that express these kinases, including acute lymphocytic leukemia and certain solid tumors.

Imatinib is sold in the U.S. by Novartis as Gleevec™ capsules containing imatinib mesylate equivalent to 100 or 400 mg of imatinib free base.

U.S. Pat. No. 5,521,184 and WO 03/066613 describe synthetic routes for preparing imatinib. One synthetic process, depicted in Scheme 1, involves reacting 4-(4-methyl-piperazin-1-ylmethyl)-benzoic acid methyl ester with 3-nitro-4-methyl-aniline to obtain N-(4-methyl-3-nitrophenyl)-4-(4-methyl-piperazin-1-ylmethyl)-benzamide, which is subsequently reduced to obtain N-(3-amino-4-methyl-phenyl)-4-(4-methyl-piperazin-1-ylmethyl)-benizamide. The latter is reacted with cyanamide ($NH_2CN$) in a mixture of concentrated hydrochloric acid solution and n-butanol to produce N-(3-guanidino-4-methyl-phenyl)-4-(4-methyl-piperazin-1-ylmethyl)-benzamide, which is subsequently reacted with 3-dimethylamino-1-pyridin-3-yl-propenone to obtain imatinib.

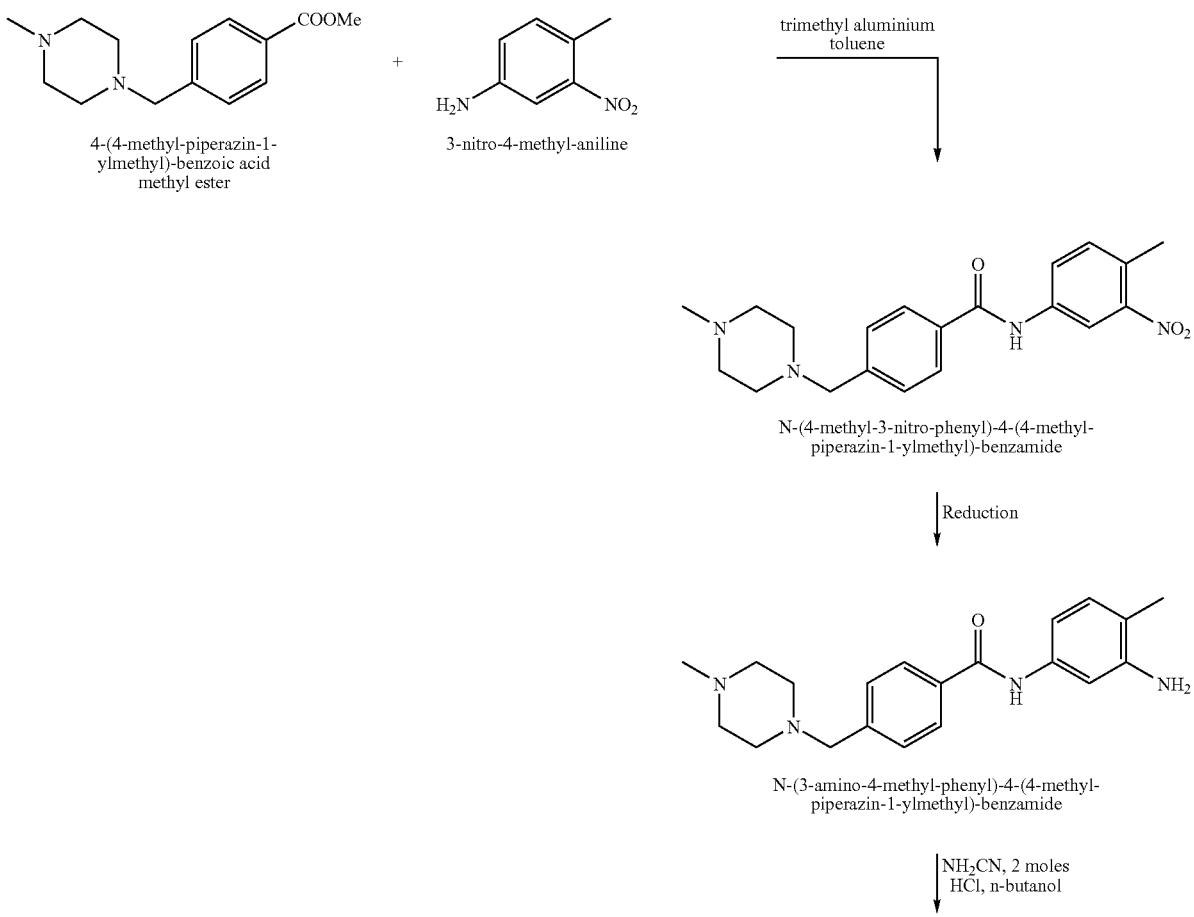

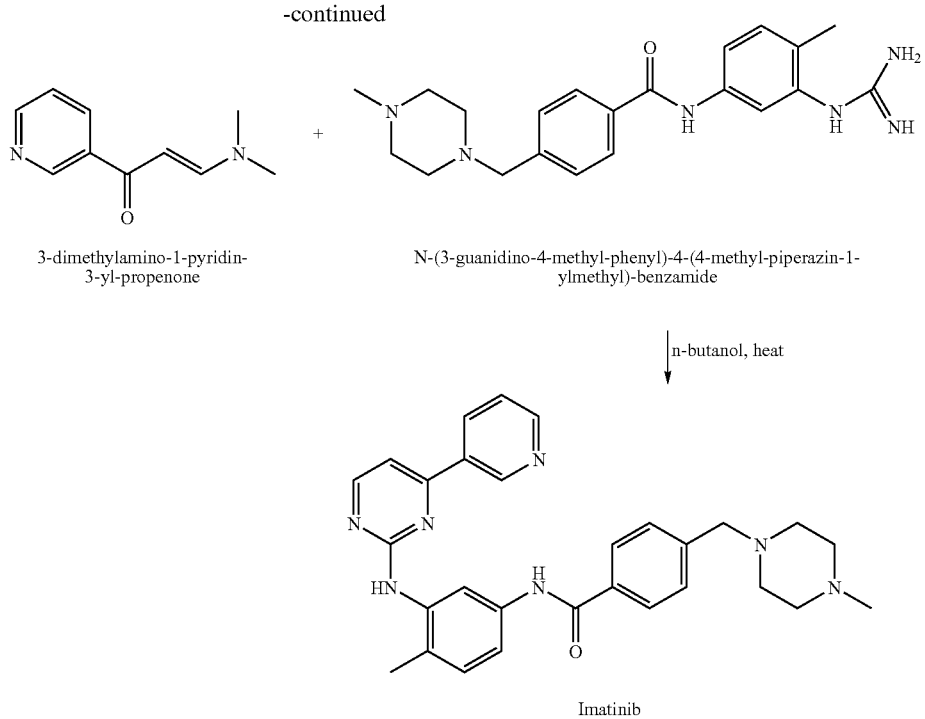

Another process, depicted in Scheme 2, involves reacting 3-bromo-4-methyl-aniline with 4-(4-methyl-piperazin-1-yl-methyl)-benzoic acid methyl ester to obtain N-(3-bromo-4-methyl-phenyl)-4-(4-methyl-piperazin-1-ylmethyl)-benzamide. The latter is reacted with 4-(3-pyridyl)-2-pyrimidine amine (which is obtained by reacting cyanamide with 3-dimethylamino-1-pyridin-3-yl-propenone) to obtain imatinib.

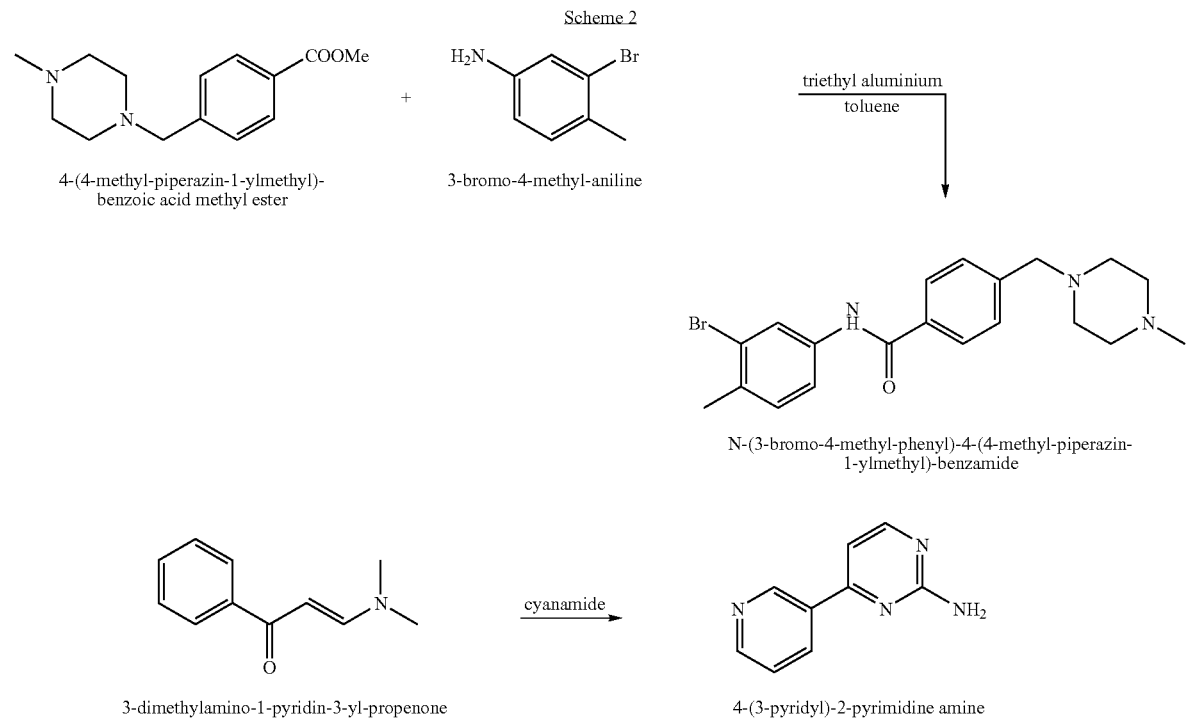

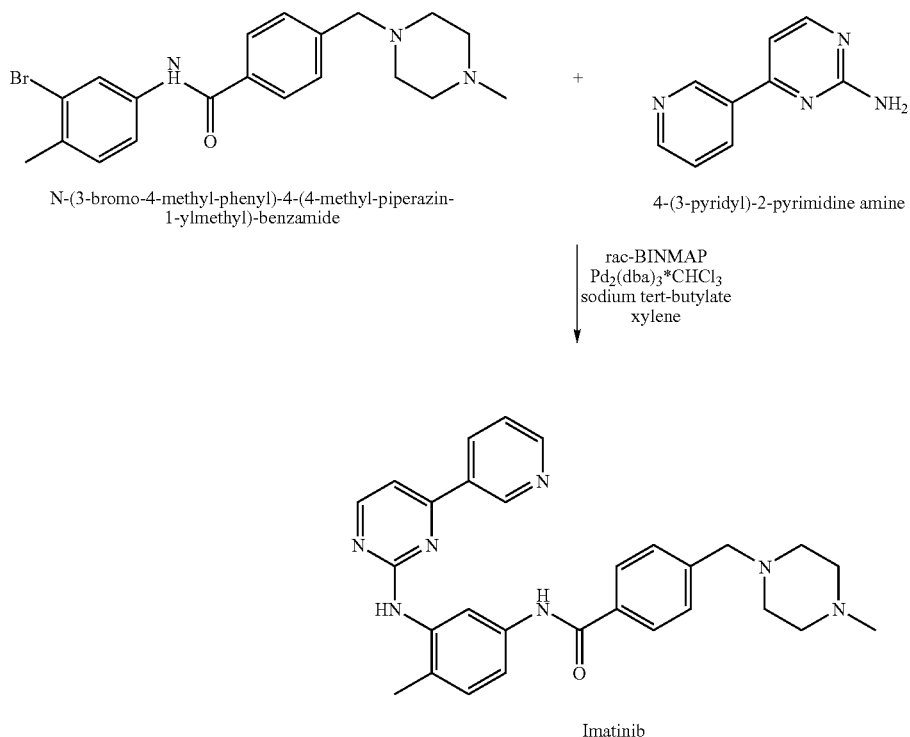

Yet another process, depicted in Scheme 3, includes obtaining 2-methyl-5-nitrophenyl-guanidine from 2-amino-4-nitro-toluene by adding nitric acid to a solution of the latter in ethanol followed by addition of cyanamide. The product is subsequently reacted with 3-dimethylamino-1-pyridin-3-yl-propenone to obtain N-(2-methyl-5-nitrophenyl)-4-(3-pyridyl)-2-pyrimidine-amine, which is subsequently reduced and reacted with 4-(4-methyl-piperazinomethyl)-benzoyl chloride to obtain imatinib.

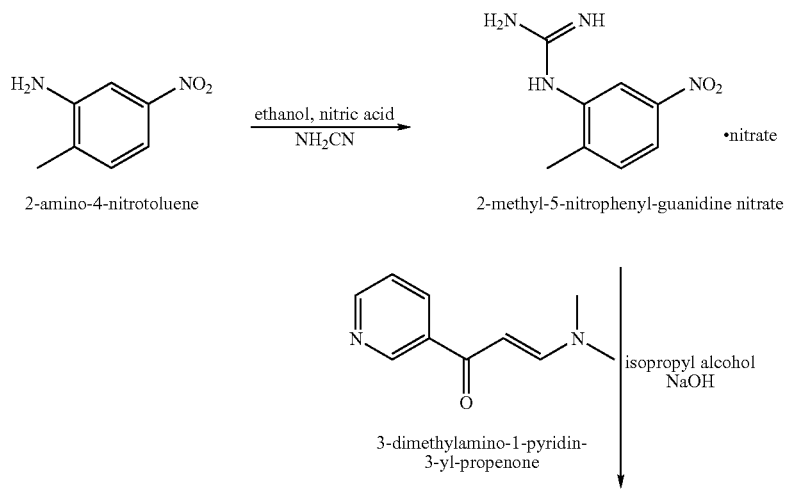

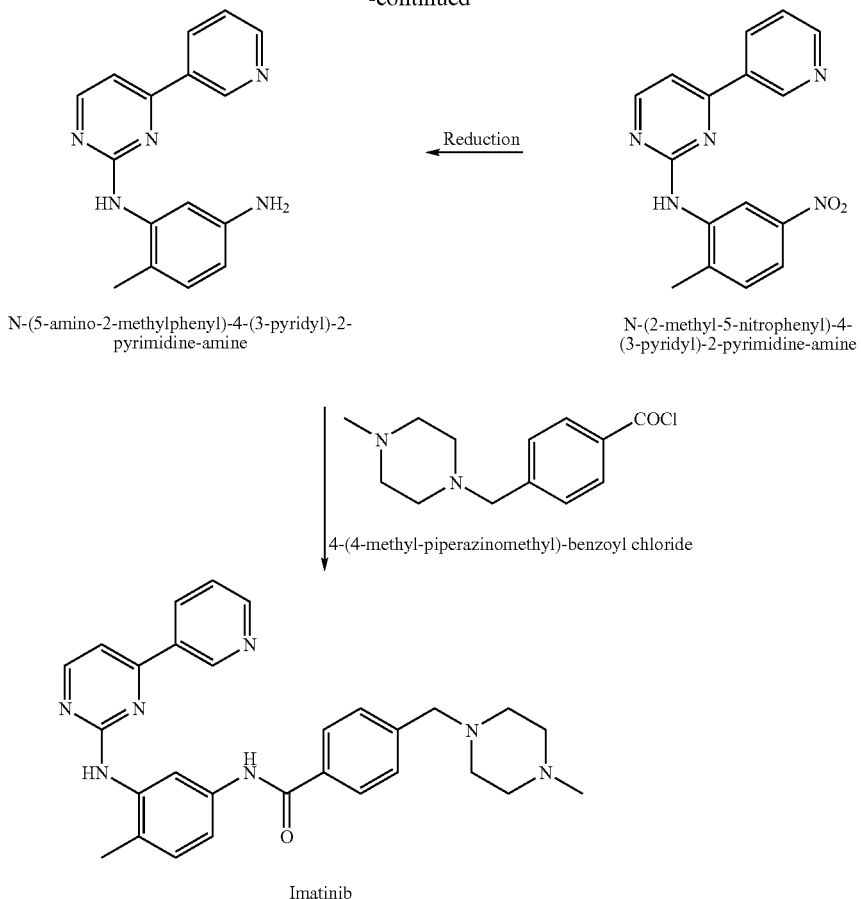

The syntheses described in U.S. Pat. No. 5,521,184 and WO 03/066613 are not particularly suitable for industrial purposes. For example, the reaction between N-(3-bromo-4-methyl-phenyl)-4-(4-methyl-piperazin-1-ylmethyl)-benzamide and 4-(3-pyridyl)-2-pyrimidine amine, which uses a reagent mixture of rac-BINAP (a phosphine oxide catalyst) and $Pd_2(dba)_3$*$CHCl_3$ (Example 10 in WO 03/066613). These catalysts are very expensive and not suitable for commercial production.

WO 2004/074502 (hereinafter the '502 application) describes a coupling reaction between N-(5-amino-2-methylphenyl)-4-(3-pyridyl)-2-pyrimidine-amine and 4-(4-methyl-piperazin-1-ylmethyl)-benzoyl chloride, wherein DMF is used instead of pyridine. However, the method described in the '502 application lacks an advantage in that the coupling reaction produces the hydrohalide salt of imatinib, e.g., imatinib trihydrochloride monohydrate, which has to be treated with a base in order to afford the imatinib base, thus an extra step is required. Further, conventional methods for coupling N-(5-amino-2-methylphenyl)-4-(3-pyridyl)-2-pyrimidine-amine require reaction with an acid halide, e.g., 4-(4-methyl-piperazin-1-ylmethyl)-benzoyl chloride, which requires an additional production step that can involve harsh and/or toxic chlorinating agents.

Thus, there is a need in the art for an imatinib production process that uses less hazardous, more environmentally friendly reagents and solvents, and uses fewer synthetic steps. The present invention provides such a process.

BRIEF SUMMARY OF THE INVENTION

The present invention provides process for preparing imatinib or a salt thereof, which process includes directly coupling 4-(4-methyl-piperazin-1-ylmethyl)-benzoic acid with N-(5-amino-2-methylphenyl)-4-(3-pyridyl)-2-pyrimidine-amine in the presence of a carboxylic acid coupling reagent, to produce imatinib, and optionally converting the imatinib into a salt. The carboxylic acid coupling reagent can include coupling reagents that are conventionally used for activating and coupling carboxylic acids. A preferred class of carboxylic acid coupling reagents are carbodiimide coupling reagents. Exemplary carbodiimide coupling reagents include N-(3-dimethylaminopropyl)-N-ethyl-carbodiimide (EDC) and salts thereof, e.g., the hydrochloride salt (EDC HCl).

In one embodiment, the process of the present invention includes:

admixing N-(5-amino-2-methylphenyl)-4-(3-pyridyl)-2-pyrimidine-amine with 4-(4-methyl-piperazine-1-ylmethyl)-benzoic acid in a solvent mixture comprising water and a first organic solvent;

adding a carboxylic acid coupling reagent (e.g., slowly, e.g., dropwise) and allowing the coupling reaction to proceed for a time period sufficient to allow substantial completion of the coupling reaction, to produce imatinib or a salt thereof;

adding a second organic solvent and a base, e.g., until a desired pH is obtained;

extracting the product (e.g., as imatinib base) with an extraction solvent and evaporating at least a portion of the organic solvent mixture;

adding a third solvent and cooling to precipitate the product (e.g., as imatinib base); and isolating the product, e.g., by collecting the precipitate, e.g., by filtration, and, optionally, washing and/or drying the precipitated product.

The process of the present invention further can include:

optionally purifying the isolated product; and optionally converting imatinib into the mesylate salt.

In accordance with the present invention, the imatinib can be purified, e.g., by crystallization. In one embodiment, the crystallization process includes:

dissolving crude imatinib in a first crystallization solvent, which can include a mixture of solvents;

evaporating at least a portion of the first crystallization solvent;

adding a second crystallization solvent to produce a crystallization solvent system and cooling to precipitate imatinib as a purified precipitate; and isolating the purified precipitate, e.g., by filtration, and, optionally, washing and/or drying the purified precipitate.

The imatinib base produced according to the present invention optionally can be converted into an imatinib salt, e.g., imatinib mesylate. In one embodiment, imatinib mesylate is prepared by reacting imatinib base with methanesulfonic acid by a process that includes:

providing a mixture of imatinib base in an organic solvent;

heating the mixture to elevated temperature and adding a solution containing methanesulfonic acid, optionally in portions;

cooling the reaction mixture sufficiently to allow crystallization of imatinib mesylate; and isolating the product, e.g., by filtration and, optionally, washing and/or drying the product.

DETAILED DESCRIPTION OF THE INVENTION

The applicants have surprisingly discovered that 4-(4-methyl-piperazin-1-ylmethyl)-benzoic acid can be coupled directly with N-(5-amino-2-methylphenyl)-4-(3-pyridyl)-2-pyrimidine-amine using a carboxylic acid coupling reagent. The process of the present invention is advantageous in that it avoids the need for using 4-(4-methyl-piperazin-1-ylmethyl)-benzoyl chloride, which requires an additional production step that can involve harsh and/or toxic chlorinating agents. The process of the present invention also avoids the need for using pyridine, which is not suitable for industrial use in view of its toxicity and acrid odor. The present invention thus provides a process for preparing imatinib or a salt thereof, which process includes reacting 4-(4-methyl-piperazin-1-ylmethyl)-benzoic acid with N-(5-amino-2-methylphenyl)-4-(3-pyridyl)-2-pyrimidine-amine in the presence of a carboxylic acid coupling reagent, to produce imatinib, and optionally converting the imatinib into a salt.

Suitable carboxylic acid coupling reagents include N-(3-dimethylaminopropyl)-N-ethyl-carbodiimide (EDC, as a free base or as hydrochloride), 2-(5-norborene-2,3-dicarboximido)-1,1,3,3-tetramethyluronium tetrafluoroborate, 4-(4,6-dimethoxy-1,3,5-triazin-2-yl)-4-methylmorpholinium chloride, 2-[(ethylcarbonimidoyl)amino-N,N,N-trimethylethaneaminium iodide, N'-(ethylcarbonimidoyl)-N,N-dimethyl-1,2-ethaneamine (as a base or a hydrochloride), and the like. A preferred class of carboxylic acid coupling reagents are carbodiimide coupling agents. Exemplary carbodiimide coupling agents include N-(3-dimethylaminopropyl)-N-ethyl-carbodiimide (EDC) and salts thereof, e.g., the hydrochloride salt (EDC HCl).

An exemplary embodiment of the present invention is depicted in Scheme 4 below.

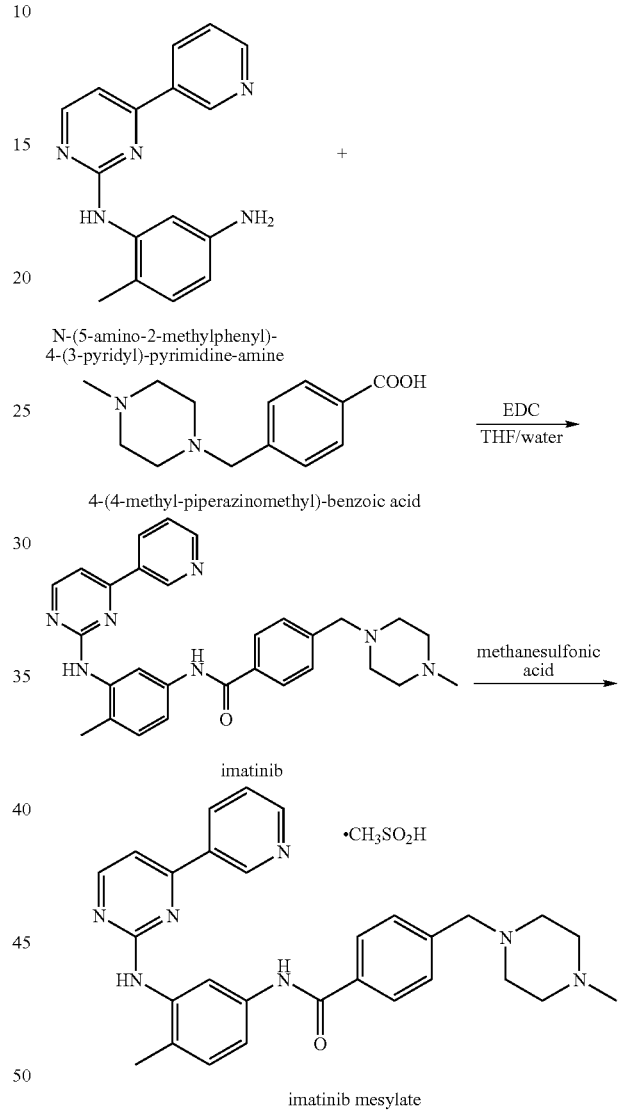

In one embodiment of the present invention, the coupling reaction is carried in an aqueous solvent mixture. Exemplary aqueous solvent mixtures in which the coupling reaction can be carried out include solvent mixtures of one or more organic solvents, e.g., THF, and water. Thus, imatinib or a salt (e.g., addition salt) thereof can be obtained by directly reacting N-(5-amino-2-methylphenyl)-4-(3-pyridyl)-2-pyrimidine-amine with 4-(4-methyl-piperazine-1-ylmethyl)-benzoic acid in the presence of a carboxylic acid coupling reagent (e.g., EDC or a salt thereof), in a solvent mixture that includes, e.g., water and THF, at ambient temperature to yield highly pure imatinib base.

In one embodiment, the process of the present invention includes:

admixing N-(5-amino-2-methylphenyl)-4-(3-pyridyl)-2-pyrimidine-amine with 4-(4-methyl-piperazine-1-ylmethyl)-benzoic acid in a solvent mixture comprising water and a first organic solvent;

adding a carboxylic acid coupling reagent (e.g., slowly, e.g., dropwise) and allowing the coupling reaction to proceed sufficiently to allow substantial completion of the coupling reaction, to produce imatinib or a salt thereof;

adding a second organic solvent and a base, e.g., until a desired pH is obtained;

extracting the product (e.g., as imatinib base) with an extraction solvent and evaporating at least a portion of the organic solvent mixture;

adding a third solvent and cooling to precipitate the product (e.g., as imatinib base); and isolating the product, e.g., by collecting the precipitate, e.g., by filtration, and, optionally, washing and/or drying the precipitated product.

The first organic solvent can include, e.g., tetrahydrofuran (THF), 2-methyltetrahydrofuran, acetonitrile, N,N-dimethylformamide (DMF), dimethylacetamide (DMA), dimethylsulfoxide (DMSO), N-methyl-2-pyrrolidone (NMP), or a mixture thereof. A particularly preferred first organic solvent is THF.

The organic solvent:water ratio (e.g., the THF:water ratio) in the solvent mixture in which the coupling reaction is performed can vary, e.g., from about 1:1 (v/v) to about 1:10 (v/v), e.g., about 1:2 (v/v), about 1:3 (v/v), about 1:4 (v/v), about 1:5 (v/v), about 1:6 (v/v), etc. An exemplary organic solvent:water ratio (e.g., the THF:water ratio) in the coupling reaction solvent mixture is about 1:1.5 (v/v).

The second organic solvent, added together with the base, can include, e.g., methanol, ethanol, 1-propanol, 2-propanol, 1-butanol, 2-butanol, dichlioromethane, chloroform, or a mixture thereof. An exemplary second organic solvent is a mixture of ethanol and dichloromethane.

The base can include, e.g., ammonia, sodium hydroxide, lithium hydroxide, potassium hydroxide, or a combination thereof. An exemplary base is sodium hydroxide.

The extraction solvent can include, e.g., methanol, ethanol, 1-propanol, 2-propanol, ethyl acetate, dichloromethane, chloroform, toluene, and mixtures thereof. Ali exemplary extraction solvent is a mixture of ethanol and dichloromethane. The ethanol:dichloromethane ratio in the extraction solvent can vary, e.g., from about 1: 1 (v/v) to 1:10, e.g., about 1:2 (v/v), about 1: 3 (v/v), about 1:4 (v/v), about 1:5 (v/v), about 1:6 (v/v), etc. An exemplary ethanol:dichloromethane ratio for the extraction solvent is 1:4 (v/v).

The third solvent can include, e.g., $C_1$-$C_4$ alcohols, e.g., methanol, ethanol, 1-propanol, 2-propanol, 1-butanol, 2-butanol, isobutanol, and the like, and mixtures thereof. An exemplary third solvent includes ethanol.

The crude imatinib base obtained in accordance with the present invention preferably has a purity of at least about 98.5%, and more preferably has a purity at least about 99.2%.

The process of the present invention further can include:
optionally purifying the isolated/crude product; and
optionally converting the imatinib into a salt, e.g., the mesylate salt.

The imatinib base can be purified by any conventional method known in the art such as, for example, precipitation, crystallization, slurrying, washing in a suitable solvent, column chromatography, dissolution in an appropriate solvent (e.g., dichloromethane) and re-precipitation by addition of a second solvent in which the compound is insoluble, or any combination of such methods.

In one embodiment, the imatinib is optionally purified by crystallization. An exemplary crystallization process includes:

dissolving crude imatinib in a first crystallization solvent, which can include a solvent mixture;

evaporating at least a portion of the first crystallization solvent;

adding a second crystallization solvent to produce a crystallization solvent system and cooling to precipitate imatinib as a purified precipitate; and isolating the purified precipitate, e.g., by filtration, and, optionally, washing and/or drying the purified precipitate.

The crystallization solvent system (e.g., the combined first and second crystallization solvents) can include, e.g., methanol, ethanol, 1-propanol, 2-propanol, dichloromethane, chloroform or a mixture thereof. An exemplary crystallization solvent system is a mixture of dichloromethane and ethanol.

The imatinib can be converted into a salt, e.g., imatinib mesylate, by reacting imatinib base with a suitable acid, e.g., methanesulfonic acid. An exemplary process for converting imatinib into the mesylate salt includes:

providing a mixture imatinib base in an organic solvent;

heating the mixture to elevated temperature and adding a solution containing methanesulfonic acid, optionally in portions;

cooling the reaction mixture sufficiently to precipitate imatinib mesylate, e.g., as a crystalline product; and isolating the imatinib mesylate, e.g., by filtration and, optionally, washing and/or drying the imatinib mesylate.

The solvent used for converting imatinib base into the mesylate salt can include, e.g., ethyl acetate, diethyl ether, diisopropyl ether, methyl tert-butyl ether, acetone, methyl ethyl ketone (MEK), methyl isobutyl ketone (MIBK), cyclohexanone, 4-methylcyclohexanone, or a mixture thereof. An exemplary solvent that can be used for converting imatinib base into the mesylate salt is 4-methylcyclohexanone. The 4-methylcyclohexanone:imatinib base ratio can vary from, e.g., about 1:1 (g/ml) to about 1:50(g/ml). An exemplary 4-methylcyclohexanone:inatinib base ratio is about 1:30 (g/ml). The imatinib base:methanesulfonic acid ratio can be, e.g., about 1:1 (molar ratio), thus, no excess of methanesulfonic acid is needed to obtain essentially complete conversion to the salt.

The process of the present invention preferably produces imatinib mesylate containing less than about 0.02% of the starting material N-(5-amino-2-methylphenyl)-4-(3-pyridyl)-2-pyrimidine-amine (according to HPLC).

The process of the present invention preferably produces imatinib mesylate in a purity of at least about 98.5%, and more preferably in a purity of at least about 99.5%.

The imatinib mesylate produced in accordance with the present invention can be used in a pharmaceutical composition, which can include imatinib mesylate produced as described herein (e.g., in a therapeutically effective amount) and one or more pharmaceutically acceptable additives and/or excipients.

The following examples illustrate the practice of the present invention in some of its embodiments, but should not be construed as limiting the scope of the invention. Other embodiments will be apparent to one skilled in the art from consideration of the specification and examples. It is intended that the specification, including the examples, is considered exemplary only without limiting the scope and spirit of the invention.

EXAMPLE 1

This example describes the preparation of imatinib base.

A reaction vessel was charged with 11 g (0.04 mol) of N-(5-amino-2-methylphenyl)-4-(3-pyridyl)-2-pyrimidine-amine and 13.4 g (0.044 mol) of 4-(4-methyl-piperazinomethyl)-benzoic acid at ambient temperature and 44 ml of THF and 66 ml of water were added. The mixture was stirred for about 20 minutes to obtain a solution and cooled back to ambient temperature. 9.24 g of EDC HCl was added in several portion during a period of 10 minutes and stirred for one hour.

114 ml of dichloromethane and 29 ml of ethanol were then added and the pH was adjusted to a value that ranges between 8-9 with 17.6 ml of 20% NaOH. The phases were separated and the aqueous solution was extracted with 22 ml of a 4/1 (v/v) mixture of dichloromethane and ethanol. The organic phases were combined and concentrated to about 90 ml under vacuum and 90 ml of ethanol was added followed by concentrating the volume to 80 ml. The mixture was cooled to 0-5° C. and stirred for about an hour and the thus formed solid was filtered, washed with 3×22 ml of cold ethanol and dried under vacuum to afford 15.5 g of crude imatinib in 76% yield, having a purity of 99.3%, by HPLC.

EXAMPLE 2

This example describes the crystallization of crude imatinib base. A reaction vessel was charged with 15.5 g of the crude imatinib base of example 1, and 121 ml of about 4/1 mixture (v/v) of dichloromethane/ethanol was added at ambient temperature. The insoluble matter was filtered off and the remaining solution was concentrated under vacuum. 130 ml of ethanol was added to the concentrate and the mixture was concentrated to a volume of about 130 ml. The mixture was cooled to a temperature of 0-5° C. and mixing was maintained for an hour. The mixture was filtered and the thus formed precipitate was collected by filtration and washed with 3×20 ml of ethanol and dried to afford 14.2 grams of imatinib base in 72% yield, having 99.8% purity, and containing 0.01% of the starting material N-(5-amino-2-methylphenyl)-4-(3-pyridyl)-2-pyrimidine-amine (according to HPLC).

EXAMPLE 3

This example describes the preparation of crystalline imatinib mesylate from imatinib base.

A three-necked reaction vessel equipped with a thermometer, a reflux condenser and a mixer was charged with 1.004 gram of imatinib base (2.04 mmoles) under nitrogen atmosphere and mixed with 30 ml of 4-methylcyclohexalnone. The mixture was heated to 65° C. and 375 µL of methanesulfonic acid were mixed with 30 ml of 4-methylcyclohexanone to form a solution, and 11 ml (2.04 mmoles) of the thus formed methanesulfonic acid solution was slowly added to the solution of imatinib base. At the end of the addition the obtained suspension was cooled to room temperature and the resulting wet crystals of imatinib mesylate were filtered and dried. The purity by HPLC was 99.6%.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for preparing imatinib or a salt thereof, the process comprising reacting 4-(4-methyl-piperazin-1-ylmethyl)-benzoic acid with N-(5-amino-2-methylphenyl)-4-(3pyridyl)-2-pyrimidine-amine in the presence of a carboxylic acid coupling reagent, to produce imatinib, and optionally converting the imatinib into a salt, wherein the carboxylic acid coupling reagent is a carbodiimide, 2-(5-norborene-2,3-dicarboximido)-1,1,3,3-tetramethyluronium tetrafluoroborate, 4-(4,6-dimethoxy-1,3,5-triazin-2-yl)-4-methylmorpholinium chloride, 2-[(ethylcarbonimidoyl)amino-N,N,N-trimethyl-ethaneaminium iodide, or N'-(ethylcarbonimidoyl)-N,N-dimethyl-1,2-ethaneamine or the hydrochloride salt thereof.

2. The process of claim 1, wherein the carboxylic acid coupling reagent is a carbodiimide.

3. The process of claim 2, wherein the carbodiimide is N-(3-dimethylaminopropyl)-N-ethyl-carbodiimide (EDC) or the hydrochloride salt thereof (EDC HCl).

4. The process of claim 1, wherein the carboxylic acid coupling reagent is 2-(5-norborene-2,3-dicarboximido)-1,1,3,3-tetramethyluronium tetrafluoroborate, 4-(4,6-dimethoxy-1,3,5-triazin-2-yl)-4-methylmorpholinium chloride, 2-[(ethylcarbonimidoyl)amino-N,N,N-trimethyl-ethaneaminium iodide, or N'-(ethylcarbonimidoyl)-N,N-dimethyl-1,2ethaneamine or the hydrochloride salt thereof.

5. The process of claim 1, wherein the coupling reaction is carried out in an aqueous solvent mixture.

6. The process of claim 1, comprising:
admixing N-(5-amino-2-methylphenyl-4-(3-pyridyl)-2-pyrimidine-amine with 4-(4-methyl-piperazine-1-ylmethyl)-benzoic acid in a solvent mixture comprising water and a first organic solvent;

adding the carboxylic acid coupling reagent and allowing the coupling reaction to proceed to substantial completion to produce imatinib or a salt thereof;
adding a second organic solvent and a base;
extracting the product with an extraction solvent and evaporating at least a portion of the solvent mixture;
adding a third solvent and cooling to precipitate the product; and
isolating the product.

7. The process of claim 6, further comprising:
purifying the isolated product; and
optionally converting imatinib into the mesylate salt.

8. The process of claim 6, wherein the first organic solvent is tetrahydrofuran (THF), 2-methyltetrahydrofuran, acetonitrile, N,N-dimethylformamide (DMF), dimethylacetamide (DMA), dimethylsulfoxide (DMSO), N-methyl-2-pyrrolidone (NMP), or a mixture thereof.

9. The process of claim 8, wherein the first organic solvent is THF.

10. The process of claim 9, wherein the THF:water ratio in the solvent mixture is about 1:1.5 (v/v).

11. The process of claim 6, wherein the second organic solvent is methanol, ethanol, 1-propanol, 2-propanol, 1-butanol, 2-butanol, dichloromethane, chloroform, or a mixture thereof.

12. The process of claim 11, wherein the second organic solvent is a mixture of ethanol and dichloromethane.

13. The process of claim 6, wherein the base is ammonia, sodium hydroxide, lithium hydroxide, potassium hydroxide, or a combination thereof.

14. The process of claim 13, wherein the base is sodium hydroxide.

15. The process of claim 6, wherein extraction solvent is methanol, ethanol, 1-propanol, 2-propanol, ethyl acetate, dichloromethane, chloroform, toluene, or a mixture thereof.

16. The process of claim 15, wherein the extraction solvent is a mixture of ethanol and dichloromethane.

17. The process of claim 16, wherein the ethanol:dichloromethane ratio in the extraction solvent is 1:4 (v/v).

18. The process of claim 6, wherein the third solvent is methanol, ethanol, 1-propanol, 2-propanol, 1-butanol, 2-butanol, isobutanol, or a mixture thereof.

19. The process of claim 18, wherein the third solvent is ethanol.

20. The process of claim 7, wherein the isolated product is purified by a crystallization process comprising:
dissolving the isolated product in a first crystallization solvent;
evaporating at least a portion of the first crystallization solvent;
adding a second crystallization solvent to produce a crystallization solvent system and cooling to precipitate imatinib as a purified precipitate; and
isolating the purified precipitate.

21. The process of claim 20, wherein the crystallization solvent system comprises methanol, ethanol, 1-propanol, 2-propanol, dichloromethane, chloroform or a mixture thereof.

22. The process of claim 21, wherein the crystallization solvent system is a mixture of dichloromethane and ethanol.

23. The process of claim 7, comprising reacting imatinib base with methanesulfonic acid to produce imatinib mesylate.

* * * * *